US009050382B2

(12) United States Patent  
Carr

(10) Patent No.: US 9,050,382 B2  
(45) Date of Patent: Jun. 9, 2015

(54) CLOSE PROXIMITY AIRBORNE INFLUENZA/PATHOGEN MITIGATOR

(71) Applicant: Peter Carr, Cary, NC (US)

(72) Inventor: Peter Carr, Cary, NC (US)

(*) Notice: Subject to any disclaimer, the term of this patent is extended or adjusted under 35 U.S.C. 154(b) by 0 days.

(21) Appl. No.: 14/199,060

(22) Filed: Mar. 6, 2014

(65) Prior Publication Data

US 2014/0363333 A1   Dec. 11, 2014

Related U.S. Application Data

(60) Provisional application No. 61/777,106, filed on Mar. 12, 2013.

(51) Int. Cl.
| | |
|---|---|
| *A61L 2/08* | (2006.01) |
| *A62B 7/08* | (2006.01) |
| *A61L 9/00* | (2006.01) |
| *B01L 1/04* | (2006.01) |
| *A61L 9/16* | (2006.01) |
| *A61L 9/02* | (2006.01) |
| *A61L 9/03* | (2006.01) |

(52) U.S. Cl.
CPC ... *A61L 9/16* (2013.01); *A61L 9/02* (2013.01); *A61L 9/03* (2013.01)

(58) Field of Classification Search
CPC ............... A61L 2/00; A61L 2/18; A61L 9/00; A61L 9/03
USPC ................... 422/1, 26, 28, 33, 123–124, 306; 454/187, 228
See application file for complete search history.

(56) References Cited

U.S. PATENT DOCUMENTS

| | | | |
|---|---|---|---|
| 983,877 A | | 2/1911 | Cummings |
| 2,507,634 A | * | 5/1950 | Hill ............................... 454/231 |
| 3,442,230 A | | 5/1969 | Polen |
| 3,511,162 A | | 5/1970 | Truhan |
| 3,721,067 A | | 3/1973 | Agnew |
| 3,776,121 A | | 12/1973 | Truhan |
| 3,821,413 A | | 6/1974 | Hellyer |
| 4,038,974 A | | 8/1977 | Pielkenrood |
| 4,248,162 A | | 2/1981 | Skeist |
| 4,623,367 A | | 11/1986 | Paulson |
| 4,788,905 A | | 12/1988 | Von Kohorn |
| 5,086,692 A | | 2/1992 | Welch et al. |
| 5,350,337 A | | 9/1994 | Kondo et al. |
| 6,210,267 B1 | | 4/2001 | Long et al. |
| 6,217,437 B1 | | 4/2001 | Murray et al. |
| 6,471,754 B2 | | 10/2002 | Ammouri |
| 6,884,158 B1 | | 4/2005 | Blomqvist et al. |
| 6,916,238 B2 | | 7/2005 | Korman |
| 2004/0007904 A1 | | 1/2004 | Lin et al. |

\* cited by examiner

*Primary Examiner* — Monzer R Chorbaji

(74) *Attorney, Agent, or Firm* — David M. Krasnow; Nexsen Pruet, LLC

(57) ABSTRACT

Close proximity, including conversations at closer than three (3) feet apart, facilitates disease transfer via airborne pathogens. This transfer can be mitigated by the present invention, which is directed towards methods, systems and apparatuses to produce a predictably shaped and minimally intrusive air barrier that may comprise an airborne disinfectant, to divert and or render harmless and to divert and negate close proximity airborne pathogens, such as influenza and severe acute respiratory syndrome, etc., and other airborne particulates transferred from an infected person towards the face of an unfortunate recipient at normal conversational distances apart from each other, and/or to divert and render harmless such airborne particulates.

37 Claims, 7 Drawing Sheets

CLOSE PROXIMITY AIRBORNE INFLUENZA/PATHOGEN MITIGATOR

CROSS-REFERENCE

This application claims benefit of priority of U.S. Provisional Patent Application Ser. No. 61/777,106 filed Mar. 12, 2013, and incorporated by reference herein as if made a part of the present disclosure.

FIELD

The present invention is directed towards preventing the transmission of airborne pathogens between individuals. More specifically, the present invention is directed to apparatuses and methods designed to divert and/or to render harmless pathogens transferred by exhalation/inhalation from one person to another while at normal conversational distances apart. Typically, this transfer of pathogen particles is in the form of a plume directed towards the face of the unfortunate recipient.

BACKGROUND

With the urgent need to prepare for potential pandemics stemming from avian influenza, swine influenza, Severe Acute Respiratory Syndrome (SARS) and other expiratory pathogenic particles, much has been done to elucidate transmission mechanisms, the nature of the biological threat and subsequent vaccine development and distribution. However, much still has to be accomplished in regards to protecting the public at large should such a fast moving pandemic occur. It is understood that in the laboratory environment virulent pathogens are routinely handled without safety issues using isolation, very efficient masks or self-contained air breathing apparatus. However, within the realm of the general public such methods are impractical. Many of the particles concerned are less than about 1 micron in size and this is well beyond the capability of a dust mask or even a surgical mask to filter out.

Particles of less than about 5 microns in aerodynamic diameter are often termed aerosols and can be very infectious since they can travel down into the alveolar region of the lungs. It is not only sneezing and coughing that discharge such pathogens into the air but normal exhalation also releases pathogens and these tend to be in the deleterious 1 micron or less size. With normal breathing these particles are traveling at nowhere near the velocity of a cough or sneeze, but because of their small size and low settling velocity they remain airborne for considerable time and can easily reach the breathing zone of other parties at conversational distances apart. Coughing or sneezing typically produce larger particles that penetrate as far as the tracheobronchial region and, as such, can also prove to be very infectious. These larger particles tend to drop out of the air quite rapidly but not rapidly enough so as not to be a threat at normal conversational distances (e.g. up to 3 feet, etc.). For instance, in the case of SARS, the CDC (Centers for Disease Control and Prevention) recommends keeping more than three feet apart to minimize direct droplet transfer. This is also the case for droplet transfer involving other communicable diseases. Conversational distances are typically three feet or less, so protection is also needed from droplet transfer.

While potential pandemics illustrate an extreme need for an available airborne pathogen blocking and/or destruction system method and apparatus, the abundant contagious respiratory diseases within all populations together form an even greater need. In the course of the normal influenza season, some 36,000 flu related deaths occur annually in the U.S. Vaccines may not be fully effective and, even so, more than 50% of the US population goes without this potential protection. As of today, CDC recommendations to minimize disease spread of influenza between individuals are:
1. Get vaccinated for seasonal influenza;
2. Avoid close contact with those who are sick;
3. Wash hands often in soap and water;
4. Cover mouth and nose when sneezing or coughing; and
5. Avoid touching eyes, nose and mouth.

As related to Recommendation 1, less than 50% of the U.S. population receive vaccinations against influenza, leaving the balance without protection. Recommendation 2 is somewhat subjective and, as a practical matter, almost impossible to accomplish in many workplace settings. Face-to-face conversation is how business is often conducted, and knowing the state of health of the person opposite is often impossible to determine. In many cases individuals can be infectious before significant signs of illness are manifested. Even if the person opposite appears to be infectious, then telling that person to move away and hopefully go home is challenging, and can result in a loss of business productivity, and potentially is too late since the damage may already have been done.

SUMMARY OF THE INVENTION

In one embodiment, the present invention is directed towards flexible and non-intrusive apparatuses, systems and methods to prevent direct pathogen airborne contamination from one person to another, preferably while positioned opposite, or substantially opposite from each other, such as, for example, at a desk or similar workstation. For purpose of this disclosure, it is understood that the term "pathogen" includes any airborne particulate including, for example, bacteria, viruses, spores, as well as any chemical molecules, such as scents and odors emitted from a person such as, for example perfume, etc. The preferred apparatus occupies minimal desk/workstation top space, sits on and preferably requires no permanent attachment to the desk/workstation (i.e. is removably located, or portable), is fully integrated requiring only an electrical power connection (although units comprising a DC power source are also contemplated) and as such is readily portable for use where needed.

Therefore, one embodiment of the present disclosure is directed to a method of producing a predetermined stream of flowing air and directing the flowing air to a predetermined area between individuals located a predetermined distance apart comprising the steps of providing an apparatus comprising a means for producing a substantially sustained predetermined airflow to establish an air barrier, providing at least two individuals spaced apart from one another by a predetermined distance, powering the apparatus to produce an air barrier; and establishing the air barrier between the individuals, wherein the air barrier does not impinge on the individuals. The cross-section of the air barrier produced preferably comprises a substantially elliptical orientation.

A further embodiment of the present disclosure is directed to an apparatus for producing a stream of flowing air between individuals, said apparatus comprising a means for producing a substantially sustained predetermined airflow to establish an air barrier between at least two individuals spaced apart from one another by a predetermined distance. According to one embodiment, the apparatus comprising a means for pressurizing air and producing the air barrier does not impinge on the individuals, or preferably is not perceived or sensed by the individuals. The cross-section of the air barrier produced preferably comprises a substantially elliptical orientation.

Still further, the present disclosure is directed to a method for diverting airborne pathogens comprising the steps of providing a source of airborne pathogens, said source comprising a first airflow having a first force in a first direction, providing a means of producing a second airflow having a second force, with the means able to direct the second airflow in a second direction and wherein the second direction is different from the first direction, and the second airflow intersects said first airflow, and wherein said second force is greater than said first force. The cross-section of the second airflow preferably comprises a substantially elliptical orientation.

The term "elliptical", or "substantially elliptical" for purposes of the present disclosure refers to any regular or irregular shape where a length in a first direction is greater than a length in a second direction. In other words, the use of the term "elliptical" herein captures any shape that is non-circular, including traditionally elliptical shapes formed by the presence of multiple foci.

The term "workplace" is used herein to denote any situation wherein people come together at conversational distances. This is not limited to, but includes, for example, retail counters, bank teller counters, hotel reception desks, medical facility reception desks, hospital reception counters, at the side of hospital beds between the patient and a visitor, as well as conference tables, workstations and desks in businesses and professional offices, restaurant counters and tables, public waiting areas, train stations, bus stations, airports, between adjacent seats as in theaters, aircraft or vehicles, etc.

The preferred apparatuses, systems and methods for one embodiment of the present disclosure contemplate providing an air barrier positioned between individuals on opposite sides of a desk. The purpose of the barrier is to divert the exhaled air from each party into the general air mass of the room rather than the much more direct co-mingling of the exhaled/inhaled air from both parties. When it comes to the probability of contracting an infection from an infected individual by the airborne route, proximity is of prime importance. While infections can occur from pathogens distributed within the general room air, the probability of such infection is lower as compared to the much higher probability of infection from pathogens directly transferred at conversational distances. *Ref: Aerosol Transmission of Influenza A Virus: A review of New Studies*: Raymond Tellier: *J. R. Soc.* 2009 6, S783-790 *September* 2009. A non-intrusive air barrier will eliminate this close proximity route for the spreading of infections from one individual to another.

In particular the present disclosure is directed towards an effective, and preferably portable, air barrier that can be suitably implemented in a workstation environment. The apparatuses of the present disclosure provide an air flow that is only marginally perceptible to a typical workstation user, and is therefore unobtrusive by offering a small footprint on or near to the workstation, and operates quietly, and is reliable and cost-effective.

Embodiments of this disclosure meet these requirements by providing unobtrusive apparatuses, systems and methods that deliver low absolute air flow volumes at high exit air velocities via, for example, slots, orifices or other perforations in an air distribution plenum, etc. For purposes of this disclosure, a plenum is understood to be any air filled structure that preferably receives air from a blower for distribution. The perforation pattern and/or the preferred distribution plenum is shaped so that the exiting body of air provides the desired pathogen blocking zone over the workstation. The invention can operate continuously, or can be manually activated when needed, or only operates when a presence (i.e. motion type) detector indicates that activation is needed. An inlet air muffler may also be gainfully employed to reduce noise levels at the inlet port of the system air blower.

In another preferred embodiment of this disclosure, an air disinfectant is introduced into an air stream before the air stream exits the apparatus to form the air barrier noted above. The term "air disinfectant" refers to the introduction of any agent that renders human pathogens harmless or, at a minimum, reduces the virulence of the pathogen. Air disinfectants distributed throughout the air in a room in the laboratory setting have been shown to be effective against many if not most pathogenic viruses and bacteria. However, in the real world, room air exchange rates together with mixing issues make it problematical to maintain sufficiently uniform disinfectant concentrations throughout the room air to eliminate the pathogens present. Similarly, simply reducing the overall pathogen count in the general room air has little to no effect when an infected individual breathes his or her disease-containing particles directly towards the face of the person with whom the infected individual is conversing. It is for this reason that badly contaminated rooms are generally vacated, sealed and total release foggers are used to decontaminate the air and room surfaces.

Studies in the 1940s and early 1950s "*Ref: The Bactericidal Action of Propylene Glycol Vapor on Microorganisms Suspended in the Air* O. H. Robertson et. al. *J. Exp. MED.* 1942 June 1; 75(6): 593-610" showed that various glycols, were very effective in reducing airborne pathogen counts. Most particularly, propylene glycol and triethylene glycol were shown to be lethal to airborne microorganisms in low concentrations while known to have no toxicity to humans. This lack of toxicity allows propylene glycol to be used today as an additive in everything from foods, medications, toothpaste to theatrical fogs. According to the present disclosure, well under 1 gm of propylene glycol is added to the device air stream per day. This is sufficient to provide the required kill rate of pathogens in the barrier zone, but represents a miniscule concentration when diluted in the total room air. The use of a heated wick, saturated with propylene glycol, is one non-exclusive method of delivering these small amounts of disinfectant in a controllable way, since the amount of heat to accomplish this is easily provided and may be adjusted as needed. Preferably, an amount of propylene glycol is supplied to a wick from a small reservoir that can be periodically refilled or replaced as a design feature of the device. Other disinfectants, or mixtures of one or more suitable disinfectants, that are low in toxicity may also be advantageously used. Negative ion generators may also find utility for the destruction of pathogens in the barrier zone in some applications, as may the introduction of ozone and/or radiation, such as, for example UV radiation, etc.

Heating is not the only method of adding disinfectants to the air stream. Embodiments of the present disclosure further contemplate, for example, evaporation by providing extended surface area of disinfectant across which the air flows, ultrasonic addition, injection from a high pressure disinfectant containing cartridge, micro-pump addition, etc. Even if the device is operated continuously with continuous disinfectant, addition of the total amount of disinfectant added to the general room air is inconsequential using propylene glycol or equivalent materials. However, a presence detector for controlling when the unit operates and when disinfectant is added represents a preferred operational mode.

BRIEF DESCRIPTION OF THE DRAWINGS

Figure 1:
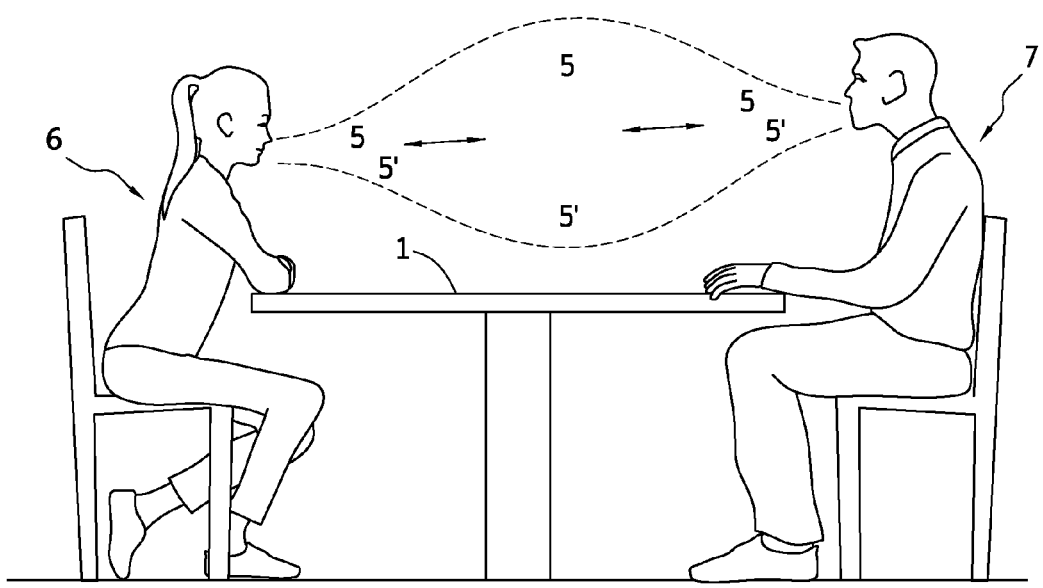
Figure 2:
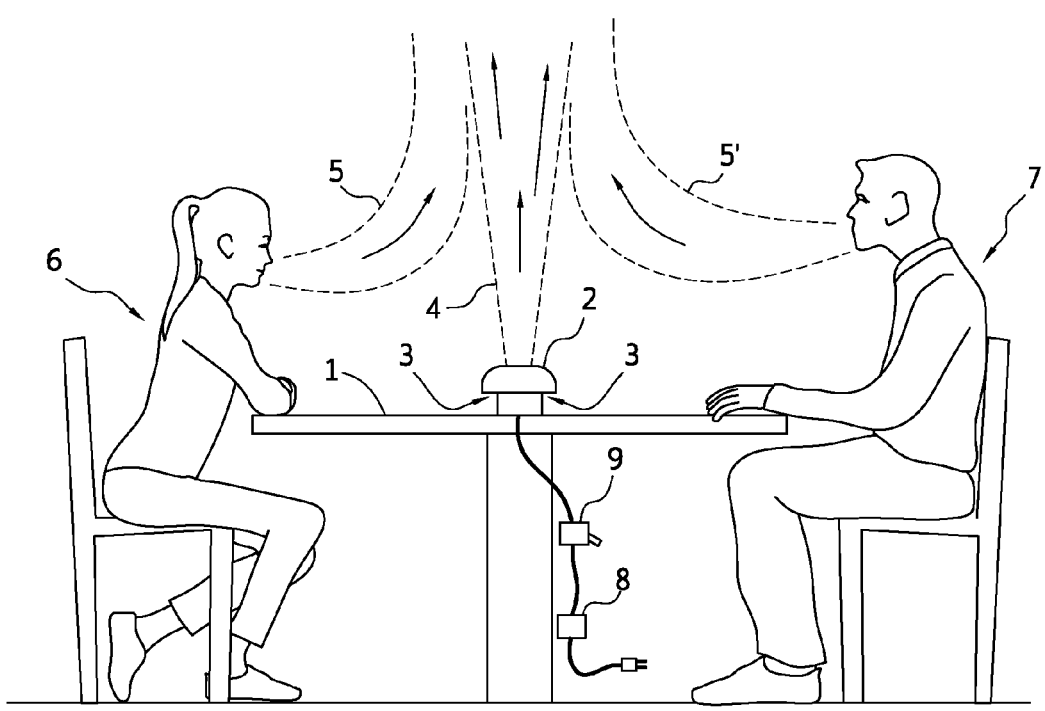
Figure 3:
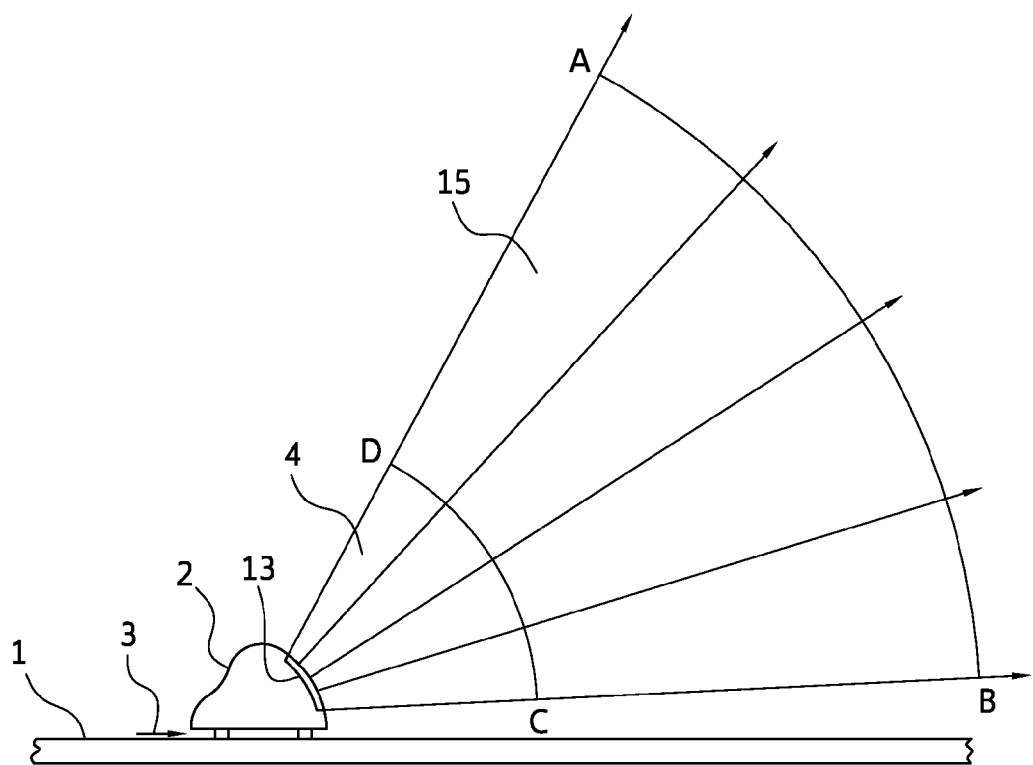
Figure 4:
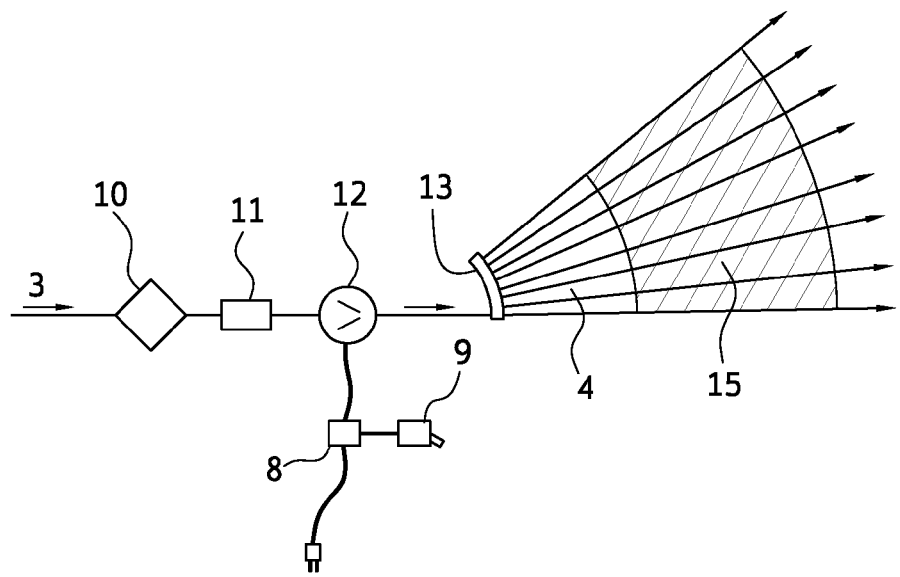
Figure 5:
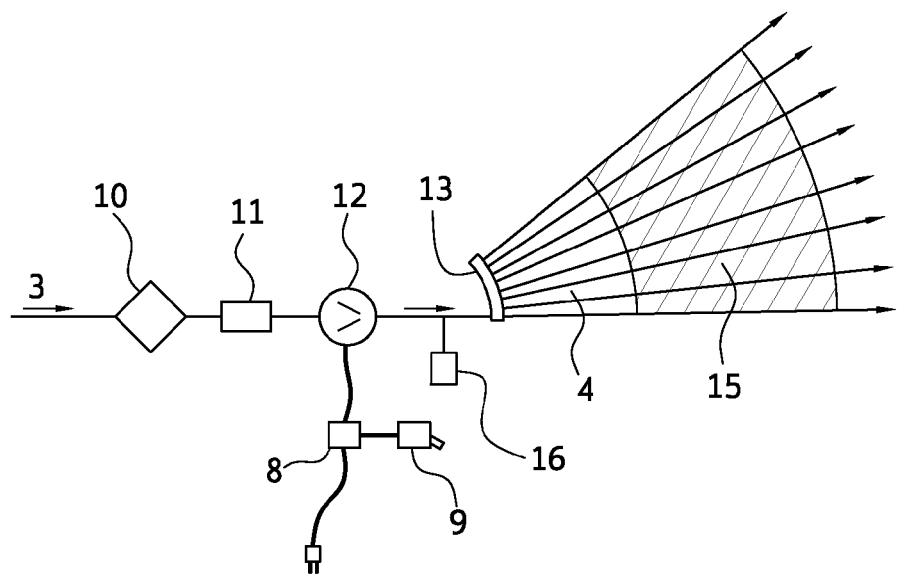
Figure 6:
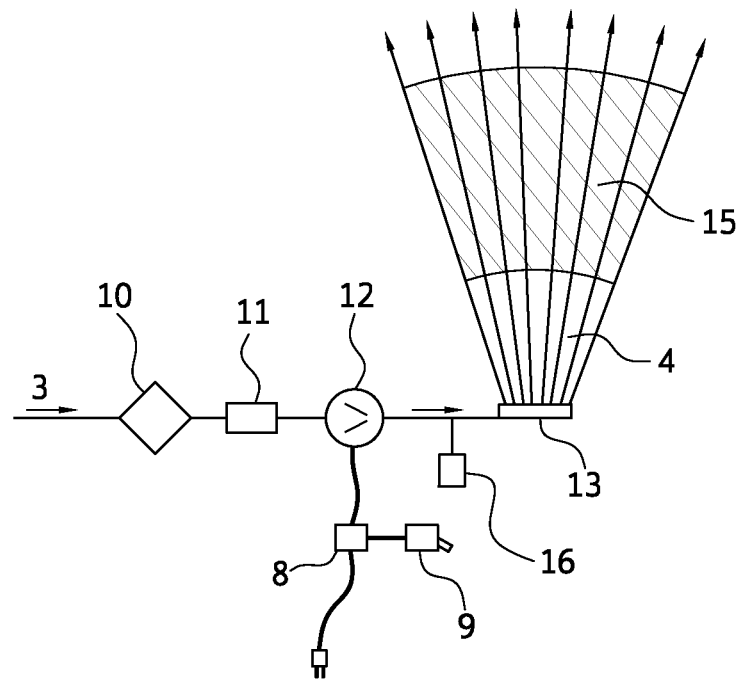
Figure 7:
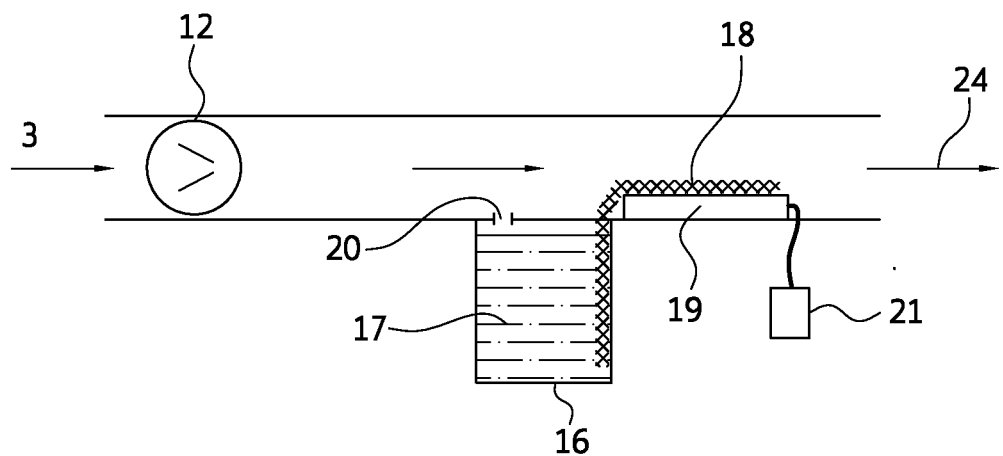
Figure 8:
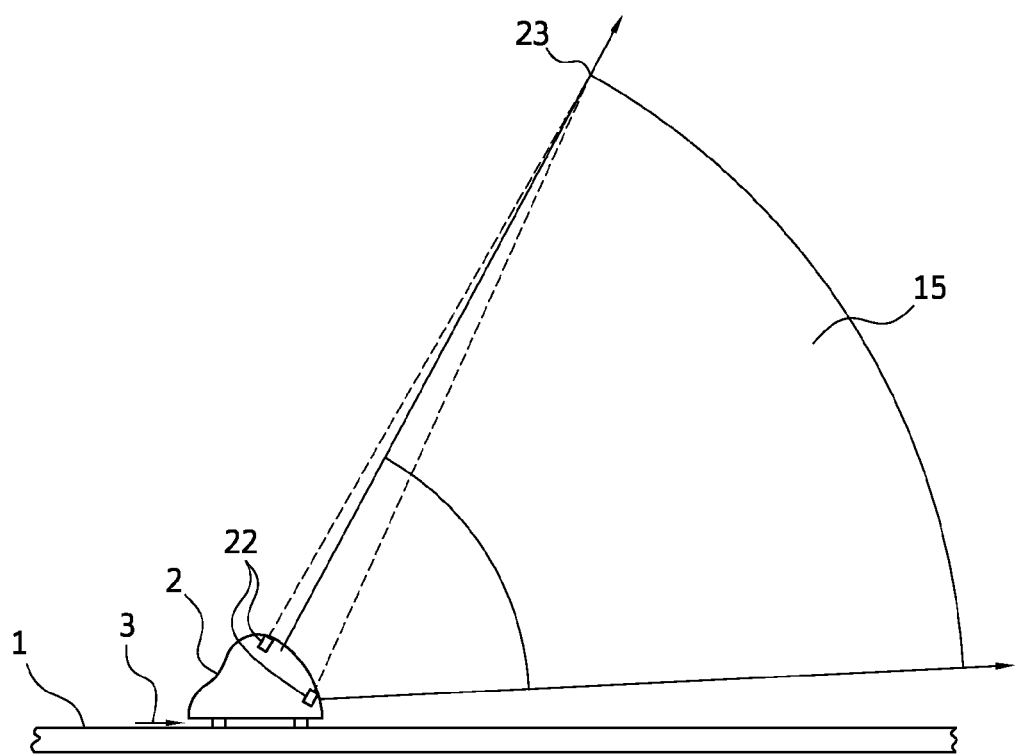
Figure 9:
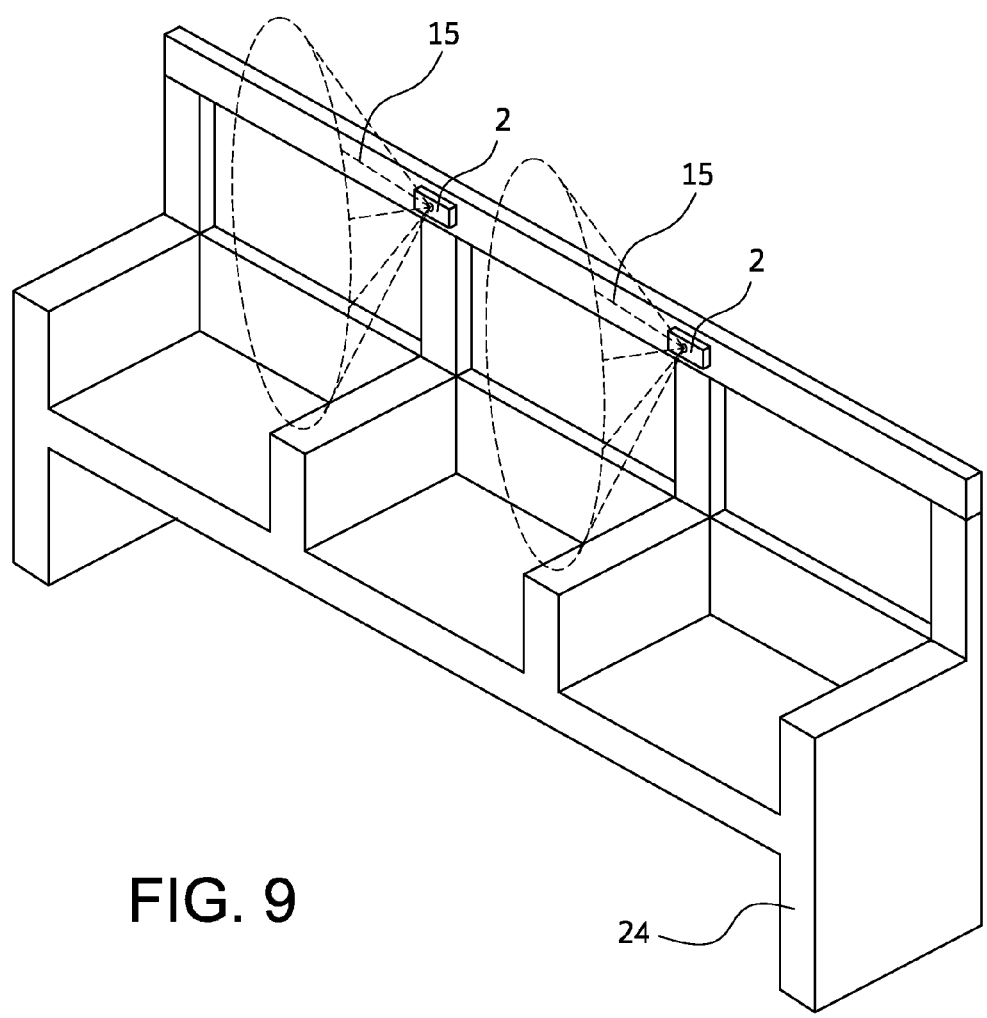

Having thus described variations of the disclosure in general terms, reference will now be made to the accompanying drawings, which are not necessarily drawn to scale and wherein:

FIG. 1 is a diagram illustrating the co-mingling of exhaled and inhaled air from two individuals at conversational distances across a desk;

FIG. 2 is a diagram of one embodiment of a preferred apparatus, system and method showing the invention preventing the direct co-mingling of exhaled and inhaled air from two individuals at conversational distances across a desk;

FIG. 3 is a diagram of one embodiment of the preferred apparatus designed to provide an unobtrusive air barrier when the apparatus is placed to the side of where the barrier zone is required;

FIG. 4 is a schematic diagram of one embodiment of a preferred apparatus, system and method showing an air distribution plenum or wand that is curved such as to deflect exhaled air at an angle between horizontal and vertical. This embodiment has particular utility if the apparatus is mounted to one side or the other of individuals conversing at a desk;

FIG. 5 is a schematic diagram of the apparatus and method in FIG. 4 with the inclusion of a disinfectant injector to add such material to the air barrier that will destroy or reduce the virulence of pathogens entering the barrier layer;

FIG. 6 is a schematic diagram of one embodiment of a preferred apparatus, system and method showing an air distribution wand designed to be centered between a desk occupant and guest. Here the air flow from the apparatus is generated substantially vertically;

FIG. 7 is a schematic diagram of one embodiment of a preferred apparatus, system and method showing a wick to transport disinfectant to a heated plate within the unit air stream;

FIG. 8 is a diagram of one embodiment of a preferred apparatus, system and method showing a visible or laser light beam as a means of identifying the upper downstream extremity of the barrier zone; and FIG. 9 is a diagram of one embodiment of a preferred apparatus, system and method to be used in conjunction with side-by-side seating arrangements.

DETAILED DESCRIPTION OF THE INVENTION

According to the present disclosure, preferred embodiments contemplate an apparatus preferably mounted such that an air flow from the device is interposed between at least two individuals to form an unobtrusive air barrier to exhaled pathogens from any individual at normal conversational distances apart. The term "unobtrusive" connotes that the air cannot flow at such a rate that the barrier zone air flow is readily sensed by the individuals and, secondly, the blower providing such flow needs to be recognized as being quiet enough for operation in close proximity to the users. This will vary somewhat depending on the background noise levels at the workstation or other location involved. Air exits from the device in such a way as to form a continuous barrier of suitable predetermined dimensions such that the exhaled air flow from each individual intersects with the barrier and is deflected.

With the understanding that the air ejected from an orifice slows and expands as it moves away from the orifice, the rate of expansion of air from a curved wand or plenum containing several orifices spaced a small distance apart from one another can be designed such that the individual air streams coalesce together at a point in advance of where the needed barrier zone starts (resulting in the desired coverage zone at the start of the barrier zone), with sufficient velocity to carry and maintain the barrier to an end point of the desired protective zone. A narrow curved slot located in the plenum may accomplish a similar air distribution profile without having to design for air intersection before the desired barrier zone starts; however, individual orifices may be more practical. Finally, the barrier zone size required and the space available on the workstation can be achieved by arranging orifices along a curved or substantially straight plenum to form the distribution plenum, for example, at an airflow rate of from about 0.15 to about 15 cubic feet per minute (cfm), and more preferably from about 0.3 to about 3.0 cfm. For example, if a barrier zone was to start 12" from the device and at the start of the barrier a width of about 12" was desired, then the straight plenum will need to be approximately 7.5" long to handle the needed row of orifices. However if only an approximate 9" wide barrier was needed at a position 12" from the device then this straight distribution plenum could be shortened to a little over 4" in length. Design considerations will determine the type of distribution plenum used but, in general, a curved plenum may result in the most compact device (e.g. the most useful footprint) especially if the design allows for the air distribution plenum to curve back and be flush, or surface-mounted in/on the air moving apparatus. If a pyramidal shaped device forms part of the design criteria, then a straight plenum may be used, as it may if a slot or space is available within or on a workstation top where a more vertical distribution of air is required or desired.

Air flow rates in the region of about 0.3 cfm are sufficient to create an acceptable barrier zone when discharged through a suitable wand. This level of air flow is barely noticeable to, for example, desk occupants. With straight plenum air distribution and three or more orifices over a 7.2" of length of plenum, this air flow will create a barrier zone that is approximately 12" wide at a position some 12" from the device and approximately 18" wide at 24" away from the device. An air distribution plenum with three or more orifices over a 2.5" length, curved to conform to a 4" radius, created a barrier zone that is wider at the 12' and 24' downstream distances from the plenum, but has a similar appearance. The above air flow rates and barrier zone sizes are examples only and not limiting on the disclosures set forth herein. The present disclosure therefore contemplates a preferred airflow rate of from about 0.15 cfm to about 15 cfm to create a preferred barrier zone. Most preferably, an airflow rate of from about 0.3 to about 3.0 cfm is established.

Using air flow rates noted above, the exit air velocity from the distribution orifices was tested at approximately 12,000 feet per minute (ft/min) and shown to form a satisfactory barrier. With a five orifice wand and 0.35 cfm total air flow rate, this necessitated an orifice size of 0.033". While not high, the several inches of water head pressure required to accomplish this exit air velocity at this orifice size is typically more than that achievable from a fan or centrifugal blower, and a positive displacement pump is likely needed. A small linear diaphragm pump such as a HIBLOW—USA™ model CD-8 air pump is suitable. Specifications for this particular pump are 0.6 cfm maximum air flow, 3 psi dead head pressure, 8.5 Watts, and importantly only 34 dBA noise, although other useful pumps may be used. At the same total air flow smaller orifices will yield higher exit velocities and enhance the barrier if necessary as will increasing the total air flow rate at the same exit velocities. However, as flow rates rise and or velocities rise, a point will be reached where a reasonable person will find the air flow and/or noise an objectionable intrusion into the workspace. High air discharge pressures to increase velocities through smaller orifices, and/or higher air flow rates, increase the work the pump has to do with the potential for increased noise. Therefore, air flow rates much over 15 cfm and/or exit air velocities in excess of 50,000 ft/min are likely to be problematical at a standard workstation.

The aforementioned air barrier eliminates the close proximity route for pathogen transmission from one individual to another. While this is the most important transmission route, it does not of itself eliminate the pathogens from the surrounding air. An example of methods to remove pathogens from the air is described in EPA-739-R-06-002 "Reregistration Eligibility Decision for Propylene Glycol and Dipropylene glycol" dated September 2006. This decision discusses the use of these glycols in aerosol sprays to continually disinfect hospital and most other types of rooms. The products were deemed safe for human respiration and product use was approved. This is to be expected since propylene glycol is safely used in a myriad of products from asthma inhalers to toothpaste to foodstuffs to theater and other smoke production to skin creams and to sterilizers. Reviewing the EPA data, the sanitizers discharged approximately 0.016 gm of propylene glycol per hour into a 6000 cubic ft. space. Assuming a minimum fresh air replacement rate of 20 cfm (ASHRE 62-2001 specifies the 20 cfm per person minimum rate) then, with full mixing the concentration of propylene glycol in the overall air will steady state at about 0.013 mg propylene glycol/ft$^3$ or about 0.16 ppm. This is a significantly lower concentration (about 300×) than the AIHA's (American Industrial Hygienists Association) suggested TWA ceiling (Time Weighted Average concentration over 8 hours). In addition, OSHA does not consider propylene glycol as hazardous by the hazard communication definition.

An additional embodiment contemplated by the present disclosure is to not only provide an air barrier to prevent direct pathogen transmission but to deactivate the pathogen in the process. With propylene glycol as the disinfectant and concentrations in the air that forms the downstream extreme of the barrier to average at least about 0.16 ppm propylene glycol/ft$^3$ of air then the exit air from the wand will need to contain about 20 ppm propylene glycol. While even the 20 ppm this is well under the TWA 8 hour ceiling, even this level dissipates rapidly dropping off to less than about 2 ppm at a mere 2" from the wand, then to about 0.3 ppm at 12" and about 0.15 ppm at 24". These very low concentrations will have the required disinfectant effect without any occupant exposure issues. Propylene glycol has a low vapor pressure at room temperature (0.05 mm Hg at 68° F.) and air saturated with vapor contains about 70 ppm propylene glycol.

Given sufficient surface area, about 20 ppm propylene glycol in the exit air is achievable by simply blowing all or part of the air over, or even bubbling the air through the glycol. Depending on the air temperature and relative humidity, water will be absorbed from the air and dilute the glycol solution. Because propylene glycol is quite hydroscopic, in air at about 68° F. and 50% relative humidity the air will add water up to about 23% by weight, at which point the solution will be at steady state. If 100% propylene glycol is used to start with, then delivery of glycol into the air will change with time as the glycol is diluted and needs to be allowed for. A more practical contemplated embodiment may include using a wick to carry glycol from a nominally sealed reservoir to a much smaller heated surface in the air stream. Simply controlling the temperature of the heated surface will dictate the glycol delivery rate to the air with very little dilution of the bulk of the glycol in the reservoir. Hot spots on any heating means are to be avoided since they may cause some glycol decomposition. A commercially available and practical way to accomplish this is to contact the wick with the hot side of a thermoelectric module (such as, for example, a thermoelectric chip, etc.), and then let the cold side dead head. Typical thermoelectric modules provide very uniform hot and cold ceramic plates where the temperatures are readily controlled. As well as being universally available, these devices operate at low voltages which add to their suitability for desk top use. The embodiment is not limited to the use of thermoelectric modules since any other uniformly heated surface that can be set at a specific temperature or controlled over a range of temperatures will suffice.

It is anticipated that the glycol reservoir will be periodically refilled as glycol is consumed or the reservoir and/or wick will be replaced, and the present disclosure contemplates the incorporation of an alert or warning signal such as, for example, a visual (blinking or constant light) or sound (buzzer, etc.) alert. In addition, the operator will generally have control as to whether he/she operates the device with air flow only or with propylene glycol added to the air. When there is a low risk of communicable disease transfer the air barrier alone may be selected but when the risk rises, for example the flu season, both the air barrier and the glycol may be chosen. Similarly a presence (e.g. motion, etc.) detector can be used to operate the device only when people are present and to do so with or without the glycol addition selected. In the instance where glycol addition is selected or de-selected the thermoelectric module offers the additional benefit of being reversible simply by changing polarity to the module. This will then create a cool rather than a hot or even room temperature wick and minimize unwanted evaporation. Note that disinfectants such as propylene glycol have a very low vapor pressure at low temperatures further minimizing evaporation. Relying on surface area alone for the required evaporation rates at room temperatures means that switching between "air only" and "air plus glycol" will typically add a movable means to direct the air over or away from the glycol/air contact surface area.

It is also understood that a preferred air barrier device, such as the one described above, with added germicide, can also provide the same function as aerosol-driven room air purifiers without adding aerosol propellant to the air along with the disinfectant. Since only about 4% of the aerosol package in commercially available air purifiers is actual disinfectant, the package has to be replaced on a regular basis (usually monthly) during continuous use. According to embodiments of the present disclosure, propellant is not required and the above device can store considerably more disinfectant for much extended replacement or, more likely, refill cycles. A maintenance cycle involving a once per year replacement or refill requires less than half a pound of glycol for the same annual dosing level. This will eliminate the twelve replacements required each year for aerosols and, as such, realize considerable maintenance and cost savings. Use of the apparatuses, systems and methods of the present disclosure in this manner will also eliminate roughly twelve pounds of polluting propellant entering the air space over the same time period.

FIG. 1 shows a schematic diagram of one typical infection transfer situation where individuals 6 and 7 are seated opposite each other across a desk or workstation top 1 in such a manner that inhaled air 5 and 5' from either individual or can contain the exhaled air from the other. The close proximity of individuals 6 and 7 can facilitate the transfer of any pathogenic particles or aerosols from one individual to the other. In FIG. 2, a preferred embodiment of the present disclosure is shown. Here, the air moving and air distribution component 2 is located on the desk or workstation top substantially between the occupants 6 and 7. Air 3 enters a blower in the air moving device 2 where it is pressurized to exit in a non-intrusive air jet 4 that intersects with and directs the so entrained occupant 6 and occupant 7 breath streams 5 and 5' into the general room air, preventing direct air contact between the occupants. The potential for infection transfer is thus substantially reduced. Power to operate the invention is shown as power supply 8, and this power may be manually or automatically controlled (e.g. turned on or off, etc.). Because embodiments of the invention contemplate a low power, portable device, it is anticipated that for some applications, preferred embodiments may comprise batteries or fuel cells for supplying power to preferred apparatuses, as well as from power outlet facilities. A timer or presence detector 9 may also be employed to operate the system only at specific times, or only when one or more occupants are present or some combination of both, etc. The location of the timer or presence detector 9 is not critical and may be integral with the air moving device 2.

While FIG. 2 shows the plane of the barrier air flow relatively equidistant from workstation occupants, it is understood that the barrier air flow can be placed closer to one occupant than another, and/or be inclined, such as by angling an air plenum, towards one or another occupant. Typically, a preferred directional orientation of the airflow will be towards a visitor for additional protection for the more "permanent" hosting occupant.

In FIG. 3, a preferred embodiment of the present disclosure shows the apparatus 2, situated on a workstation top 1. Ambient air is drawn into the system through openings on the underside of apparatus 2 (not shown) from whence it is pressurized by a blower within apparatus 2 (not shown) to be ejected into the air as an unobtrusive air stream 4 through air distribution plenum 13. This results in a barrier zone 15 with selective and predetermined boundaries ABCD. Boundary CD is application specific and can be preferably moved down to within about one or two inches of the air distribution plenum 13. However, for practical reasons, boundary CD is preferably set at an appropriate dimension so as to intersect with inhaled/exhaled are streams from workstation users. Air flow velocity decreases with distance from the air distribution plenum 13, and boundary AB represents the limits to which effective barrier zone protection can be expected. In substantially "still" air, the minimum peak air velocity at boundary AB should be about 15 ft/min or higher, and preferably in a range of from about 80 to about 240 ft/min to more easily effect the ambient air movement (circulation) within buildings. The present disclosure further contemplates even higher boundary AB air velocities may be required for specific applications, such as for example, up to about 500 ft/min or more, especially when multiple plenums are active in the device for purposes of creating multiple air barriers such as, for example, when the device is in the center of a circular workstation about which multiple occupants sit. In this arrangement (not shown), the present disclosure contemplates several air barriers being created and maintained simultaneously, in multiple directions extending out from the device 2, for example, radially.

FIG. 4 shows a block diagram of components in a preferred embodiment of the present disclosure. Air 3 is drawn into the device through air filter 10 to remove dust and/or other filterable contaminants, and then directed through an air inlet sound muffler 11 if the air blower 12 needs such a muffler to reduce device noise levels to an acceptable level. Upon leaving the blower 12, the air is transported to plenum 13 from whence it is discharged between occupants to create the pathogen barrier. The plenum can be curved or substantially straight depending on the specific barrier zone required and the space available for placing the device. The unobtrusive air stream is shown as outlet air 4 while continuing on to form the unobtrusive barrier zone 15. A power supply 8 is shown as well as the optional presence detector 9. An outlet air muffler, not shown, may also be included.

In FIG. 5, the addition of injector 16 is included in the block diagram to distribute the disinfectant into the air that forms the pathogen blocker with the balance of the system similar to that of FIG. 4. According to this variation, the choice of disinfectant and method of injection into the air can be any of those methods known to those skilled in the art. According to the present disclosure, the term "disinfectant" is understood to include the disabling and deactivation of pathogens, such as to reduce their virulence. Disinfectants include, for example, propylene glycol, dipropylene glycol, triethylene glycol, ethyl alcohol, some essential oils such as, for example, clove oil and eucalyptus oil, and various commercial preparations such as Clinister™ (dissolved in water), whether used in the pure state or as mixtures or as water based or other solvent/diluent/propellant based solutions, and alone or in combination, etc. Preferred embodiments of the present disclosure are not limited to the above disinfectants. Similarly, methods to inject the disinfectant into the air stream include, for example, passing the air over or through a pad soaked with the disinfectant with the pad being replaced when dry. The pad can also be continually fed disinfectant via a wick, small pump, or gravity feed from a disinfectant reservoir. Exposed surface area and disinfectant volatility will determine the concentration of disinfectant in the leaving air, so adjustments may be slower and more involved than desirable. Ultrasonic diffusers find widespread use in humidifiers etc. This is a further contemplated method whereby the disinfectant can be distributed into the air stream. The power level to such ultrasonic head can be adjusted to control amount and particle size of disinfectant entering the air stream for rapid adjustment. An aerosol type package containing the disinfectant and propellant can also be used, wherein the propellant distributes disinfectant into the air stream at the required rate and on/off modulation will provide adjustment as needed. In FIG. 5, the air distribution plenum is oriented to operate from the side of the occupants while in the block diagram FIG. 6 it is set to operate directly between occupants. It is also understood that the plenum may or may not be directly affixed to the main body of the device but may be remote with a connection to the main body such as, for example, an air tube, etc. An example of a useful plenum here may include a substantially flat wand mounted directly onto the workstation top or into a recess in the workstation top with an air tube connection to a remotely-sited balance of the device. Contemplated variations also provide for a multiplicity of wands/plenums with air flows provided by a single but larger balance of components. Also shown in the block diagram FIG. 6 is the power supply 8 and optional presence detector and/or timer 9 to power up the device when the workstation is occupied and/or business hours are in place. The outlet air 4 from plenum 13 is shown together with a representative barrier zone 15 and disinfectant injector 16. Inlet air 3 is also shown.

FIG. 7 is a block diagram showing a preferred method of disinfectant addition for low vapor pressure disinfectants such as propylene glycol. Here, the air exiting the device blower 12 is passed over a wick 18 that is in direct contact with, or in close communication with, a controlled heated surface 19. The wick extends from the heated surface into a disinfectant reservoir 16 and into a quantity of disinfectant 17 contained in the reservoir 16. By applying power from supply 21 to the heated surface, the disinfectant within the wick will be heated thereby increasing the driving force to distribute disinfectant into the exiting air 24. In most instances, the exiting air will not be required to be saturated with disinfectant and allow the heated surface to operate above ambient temperatures, but below the boiling point of the disinfectant. The concentration of disinfectant in the exit air can thus be closely controlled. With some disinfectants such as propylene glycol and triethylene glycol, a mist or a fog of the disinfectant in the air can be created, if desired, by using higher temperatures at heated surface 19. This type of fog is useful to visualize the air flow when positioning the device or to periodically maximize the pathogen kill rates. If it is necessary to equalize the pressure within the reservoir 16, then pressure equalizer 20 is included. It is also important that the heated surface be substantially uniformly heated since hot spots could cause some decomposition of the disinfectant. One specific controlled heated surface that can be used to accomplish this is to use the hot side of a thermoelectric module. These mass produced modules provide the required uniform surface temperature, operate at low (safe for workstation top use) DC voltages, and are readily controllable by varying the applied voltage. In addition, polarity can be reversed in the module to create a colder than ambient temperature at the wick rather than the hotter than ambient temperature with the initial polarity. At times when only the barrier is required and disinfectant is not needed, switching from a warm to a below ambient cold surface will cool the disinfectant in the wick thereby lowering its vapor pressure and minimize evaporation into the air flow. This will conserve disinfectant and increase the disinfectant replacement interval, contributing to an overall cost savings.

In FIG. 8, one preferred variation of the present disclosure shows the apparatus 2 with light beam generators 22 mounted within the apparatus such that the light beams intersect at point 23. This point 23 depicts the intended downstream boundary of barrier zone 15. This would typically be used in the positioning of the apparatus 2 on the workstation 1. While in FIG. 8, only the upper boundary is shown and identified, the lower boundary can be identified in a similar manner. LED diodes are one preferred selection for the light source(s), especially those producing colored (e.g. green, etc.) laser beams where the beam itself is more readily viewed. It is also understood that, with a suitable arrangement of mirrors, a laser in combination with a holographic plate can create a holographic image that can be projected to essentially fill and thus identify the barrier layer position. The projected image can also be tailored and dimensioned to create an additional marketing tool. It is also anticipated that a mechanical means such as, for example, a retractable rod, wire or tape can also be contained within the apparatus 2 such that when extended, the downstream boundary can be identified.

FIG. 9 shows a further embodiment of the present disclosure. Apparatus 2 is used in conjunction with and integral with side-by-side seating 24. In this embodiment, the barrier zone 15 is produced to intersect between adjacent seats to protect individuals sitting next to one another. It is understood that the mounting position of apparatus 2 is flexible depending only on the desired application such as, for example, theaters, waiting rooms/areas, aircraft seating or ground vehicular transportation seating, etc. As shown, the barrier zone 15 comprises a cross-section that is substantially elliptical in shape. It is further understood that, instead of being integral with the seating 24, apparatuses according to the present disclosure that are designed to be portable could be attached to a fixed seating area, for example, by an occupant (preferably two devices positioned on either side of the occupant), to provide a safety zone for the occupant. Because the devices can be portable, the devices can be removed by the occupant upon departing from the seated area.

Finally, by using propylene glycol or dipropylene glycol as the disinfectant, the device of this invention could readily replace the room air disinfectant methodology described in the 2006 registration approvals under EPA-739-R-06-002. Aerosol technology used to spray a measured amount of the above glycol on a timed basis such that an amount of about 0.016 gm of propylene glycol is sprayed into the room each hour. Typically, this will be accompanied by an amount of about 0.384 gm of propellant per hour as an unwanted room pollutant and the aerosol canister needing replacement on approximately a monthly schedule. With less volume than the present aerosol containers, a 0.5 lb (227 gm) container of propylene glycol in a device of the type disclosed herein would last about 14,000 hours or more than about 1.5 years without glycol maintenance. In addition, about 7.5 pounds of propellant per year would not be discharged into the room air.

Still further embodiments of the present disclosure are envisioned whereby the apparatuses, methods and systems described herein are scaled to a size (e.g. miniaturized) to facilitate their incorporation into portable personal electronic devices such as, for example, cell phones, laptop computers, calculators, etc., or even semi-permanent fixtures such as, for example, table lamps, centerpieces, chairs, etc. In addition, as stated above, while work-related and commercial environments and vehicles are contemplated for incorporating the apparatuses, systems and methods of the present disclosure, recreational settings such as personal vehicles, stadium seating at performance venues, and in-home objects are also contemplated, whereby the devices providing an air barrier may be integrated into arm rests or head rests of occupant seating. In the case of vehicles, the devices used to create the air barriers may also be incorporated into dashboards, roof areas, doors, consoles, etc.

While the preferred variations and alternatives of the present disclosure have been illustrated and described, it will be appreciated that various changes and substitutions can be made therein without departing from the spirit and scope of the disclosure. Accordingly, the scope of the disclosure should only be limited by the accompanying claims and equivalents thereof.

I claim:

1. A method of producing a predetermined stream of flowing air and directing the flowing air to a predetermined area between individuals located a predetermined distance apart comprising the steps of:
    providing an apparatus comprising a means for producing a substantially sustained predetermined airflow of from about 0.15 to about 15 cfm to establish an air barrier;
    providing at least two individuals spaced apart from one another by a predetermined distance;
    powering the apparatus to produce an air barrier; and
    establishing the air barrier between the individuals;
    wherein the air barrier does not impinge on the individuals.

2. The method of claim 1, wherein the apparatus is portable.

3. The method of claim 1, wherein at least two individuals are spaced apart from one another by a distance of from about one to about three feet.

4. The method of claim 1, wherein the air barrier comprises a substantially elliptical cross-section.

5. A method for diverting airborne pathogens comprising the steps of:

providing a source of airborne pathogens, said source comprising a first airflow having a first force in a first direction;

providing a means of producing a second airflow having an airflow rate of from about 0.15 to about 15.0 cfm, said second airflow having a second force, and said means able to direct the second airflow in a second direction;

wherein the second direction is different from the first direction, and said second airflow intersects said first airflow; and wherein said second force is greater than said first force.

6. The method of claim 5, further comprising the step of: providing a disinfecting compound to the second airflow.

7. The method of claim 6, wherein the disinfecting compound is selected from the group consisting of: propylene glycol, dipropylene glycol, triethylene glycol, ethyl alcohol, clove oil, eucalyptus oil, and combinations thereof.

8. The method of claim 6, further comprising the step of: providing a heating element in contact with the disinfecting compound.

9. The method of claim 8, further comprising the steps of: powering the heating element to produce heat; and contacting the heating element with the disinfecting compound to produce a disinfecting compound vapor.

10. The method of claim 8, wherein the heating element is a thermoelectric device.

11. The method of claim 6, further comprising the step of: providing an ultrasonic device in contact with the disinfecting compound.

12. The method of claim 5, wherein the source of airborne pathogens in the first airflow is exhaled air.

13. The method of claim 5, wherein the second airflow is an air barrier.

14. The method of claim 5, wherein the means for producing the second airflow is an air blower.

15. The method of claim 5, wherein the means for producing the second airflow comprises a reservoir containing a disinfecting compound.

16. The method of claim 5, wherein the means for producing the second airflow comprises a means selected from the group consisting of: a means for dispensing ultraviolet radiation, a means for dispensing ozone, and combinations thereof.

17. The method of claim 5, wherein the means for producing the second airflow comprises a base, said base comprising an opening through which the second airflow is directed.

18. The method of claim 5, wherein the means for producing the second airflow comprises a plenum.

19. The method of claim 18, wherein said plenum comprises a closed end and a tubular wall, and further comprising an array of orifices extending through the tubular wall.

20. An apparatus for diverting airborne pathogens in a first airflow, said airflow moving in a first direction and having a first force, said apparatus comprising:

a means of producing a second airflow having an airflow rate of from about 0.15 cfm to about 15.0 cfm, said second airflow having a second force, said means able to direct the second airflow in a second direction;

wherein the second direction is different from the first direction. and said second airflow intersects said first airflow;

wherein said second force is greater than said first force; and wherein the apparatus further comprises a disinfecting compound.

21. The apparatus of claim 20, wherein the disinfecting compound is selected from the group consisting of: propylene glycol, dipropylene glycol, triethylene glycol, ethyl alcohol, clove oil, eucalyptus oil, and combinations thereof.

22. The apparatus of claim 20, wherein the first airflow comprises exhaled air.

23. The apparatus of claim 20, wherein the second airflow is an air barrier.

24. The apparatus of claim 20, wherein the second airflow comprises a substantially elliptical cross-section.

25. The apparatus of claim 20, wherein the means for producing the second airflow is an air blower.

26. The apparatus of claim 20, wherein the means for producing the second airflow comprises a reservoir containing a disinfecting compound.

27. The apparatus of claim 20, wherein the means for producing the second airflow is selected from the group consisting of: a means for dispensing ultraviolet radiation, a means for dispensing ozone, and combinations thereof.

28. The apparatus of claim 20, wherein the means for producing the second airflow comprises a base, said base comprising an opening through which the second airflow is directed.

29. The apparatus of claim 20, wherein the means for producing the second airflow comprises a plenum.

30. The apparatus of claim 29, wherein the plenum comprises a closed end and a tubular wall, and further comprising an array of orifices extending through the tubular wall.

31. The apparatus of claim 20, wherein the apparatus further comprises:

a heating element in contact with the disinfecting compound.

32. The apparatus of claim 31, wherein the heating element is powered to produce heat.

33. The apparatus of claim 31, wherein the heating element contacts the disinfecting compound to produce a disinfecting compound vapor.

34. The apparatus of claim 31, wherein the heating element is a thermoelectric device.

35. The apparatus of claim 20, further comprising:

an ultrasonic device in contact with the disinfecting compound.

36. A vehicle comprising the apparatus of claim 20.

37. An electronic device comprising the apparatus of claim 20.

* * * * *